United States Patent [19]
Guilbault et al.

[11] 3,948,745
[45] Apr. 6, 1976

[54] ENZYME ELECTRODE

[75] Inventors: George G. Guilbault, New Orleans, La.; Glenn J. Lubrano, Raleigh, N.C.

[73] Assignee: The United States of America as represented by the Department of Health, Education and Welfare, Washington, D.C.

[22] Filed: June 11, 1973

[21] Appl. No.: 368,578

[52] U.S. Cl. ............................ 204/195 B; 204/195 P
[51] Int. Cl.² ........................................ G01N 27/46
[58] Field of Search ............ 204/1 T, 195 B, 195 P, 204/195 M, 195 G; 195/DIG. 11, 63, 68

[56] References Cited
UNITED STATES PATENTS

| 3,536,587 | 10/1970 | Stahmann et al. | 195/DIG. 11 |
| 3,539,455 | 11/1970 | Clark | 204/195 P |
| 3,542,662 | 11/1970 | Hicks et al. | 204/195 B |
| 3,623,960 | 11/1971 | Williams | 204/195 P |
| 3,666,733 | 5/1972 | Epton | 195/DIG. 11 |
| 3,707,455 | 12/1972 | Derr et al. | 204/195 P |

OTHER PUBLICATIONS

Mosbach, "Scientific America," Vol. 224, No. 3. Mar. 1971, pp. 26–33.
Bernfeld et al., "Science," Vol. 142, Nov. 1963, pp. 678 & 679.
Bareli et al., "The Journal of Biological Chemistry," Vol. 238, No. 5, May 1963, pp. 1690–1698.
Mitz et al., "Nature," Feb. 1961, Vol. 189, pp. 576 & 577.

*Primary Examiner*—T. Tung
*Attorney, Agent, or Firm*—Holman & Stern

[57] ABSTRACT

An electrode assembly for amperometric analysis of amperometrically inactive material including an enzyme for converting the inactive material to one which is amperometrically active. The enzyme is in chemically bound form to provide improved stability and is held in contact with the electrode by means of a permeable membrane.

1 Claim, 1 Drawing Figure

U.S. Patent   April 6, 1976   3,948,745
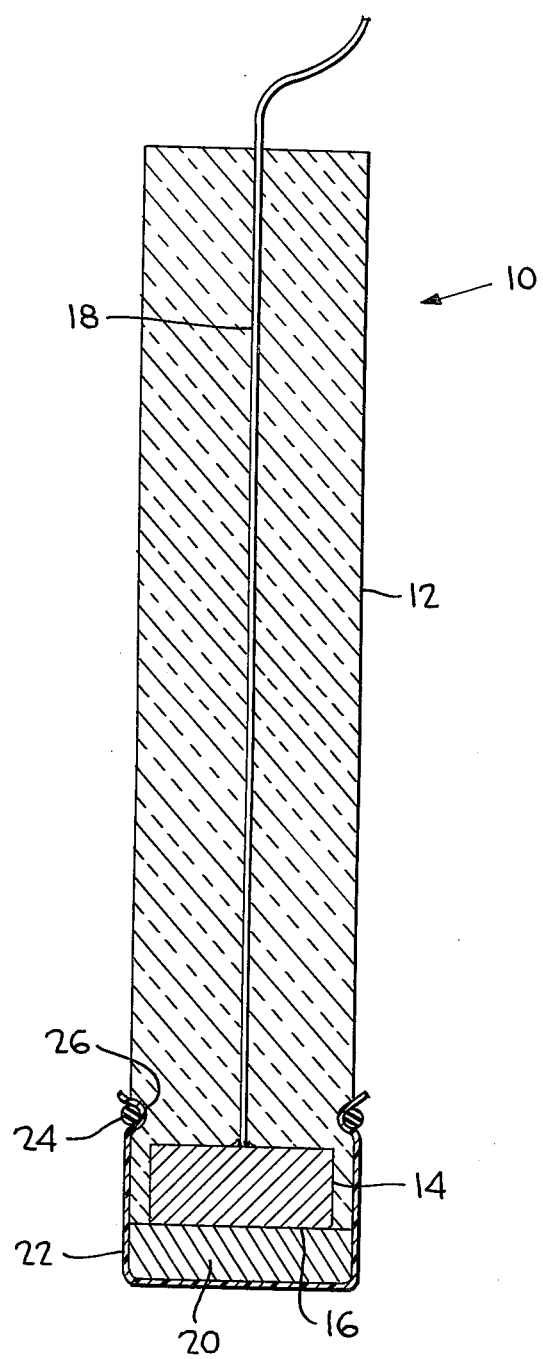

ENZYME ELECTRODE

This invention relates to an electrochemical device, and more particularly to an improved electrode structure for amperometric analysis of substances.

Amperometric electrode sensors are known which include enzymes in their structure. Such devices are employed for analyzing amperometrically inactive substances by converting them by means of enzyme catalyzed reactions into materials which are amperometrically active. For example, in the analysis of blood for glucose content, glucose, which is amperometrically inactive, is catalytically converted by the enzyme glucose oxidase in the presence of oxygen and water to gluconic acid and hydrogen peroxide. The hydrogen peroxide is amperometrically active and produces a current which is proportional to its concentration and thus to the initial concentration of glucose.

In enzyme electrodes previously employed in this manner, the enzyme has been included in the electrode structure either in the form of a solution or physically bound on a porous film having spaces large enough to hold the enzyme molecules or on a polymeric gel matrix. Such prior art electrodes have suffered from the limitation of a rather quick loss in activity with time due to the relative instability of the enzyme, requiring frequent replacement of the enzyme portion.

Accordingly, it is a primary object of the present invention to provide an improved enzyme electrode for rapid and accurate amperometric analysis.

Another object of the invention is to provide an enzyme electrode having improved enzyme stability and which retains its useful activity for longer periods of time without replacement of the enzyme portion.

The above objects are achieved in accordance with the present invention by providing an enzyme electrode wherein the enzyme is chemically bound to a solid organic material which is insoluble in the substance to be analyzed and which is held in contact with the sensing portion of the electrode by means of a membrane permeable to the material to be detected. It has been found that employing the enzyme in chemically bound form greatly improves the stability of the enzyme and slows down the loss in activity of the electrode with time to such an extent that the electrode is useful for substantially greater periods of time without replacement of the enzyme portion.

IN THE DRAWING:

FIG. 1 is an elevational sectional view of the improved enzyme electrode of the present invention.

Referring to the drawing, which illustrates a preferred embodiment of the enzyme electrode in accordance with the present invention, FIG. 1 shows an electrode assembly 10 which includes an electrically insulating support body 12 of plastic or glass which is preferably cylindrical and which supports a platinum electrode 14, the latter including an active or exposed face 16, and a conductor 18 attached to the electrode 14 and which passes through the support body 12.

Covering the exposed face 16 of the electrode 14 is a layer 20 of solid organic material having an enzyme chemically bound thereto. The layer 20 is held in contact with the exposed face 16 of the electrode 14 by means of a liquid permeable membrane 22 of cellophane or the like which is held in position on the support body 12 by an O-ring 24 or the like which fits around an annular groove or detent 26 formed on the lower end of the support body 12.

The particular enzyme employed with the electrode assembly of the present invention will depend upon the substance to be detected and will be one which is capable of reacting with the substance to produce hydrogen peroxide or other amperometrically active material to which the electrode 16 is responsive. Likewise, the particular solid organic material employed will be one which is insoluble in the substance being analyzed and capable of reacting with and chemically binding the enzyme, and will generally be a derivative of a polymeric material, such as polyacrylamide, polyacrylic acid, nylon, cellulose or the like, containing enzyme-reactive groups. For example, in an analysis for glucose content, the enzyme employed would be glucose oxidase and a suitable solid organic material to chemically bind the glucose oxidase would be a polyacrylamide derivative formed by converting a hydrazide derivative of polyacrylamide to an acyl azide intermediate that couples to amine groups on the enzyme.

Another solid organic material which is suitable for use with glucose oxidase is a diazo derivative of polyacrylic acid. It's preparation and coupling to the glucose oxidase enzyme are shown by the following reaction equations and described below:

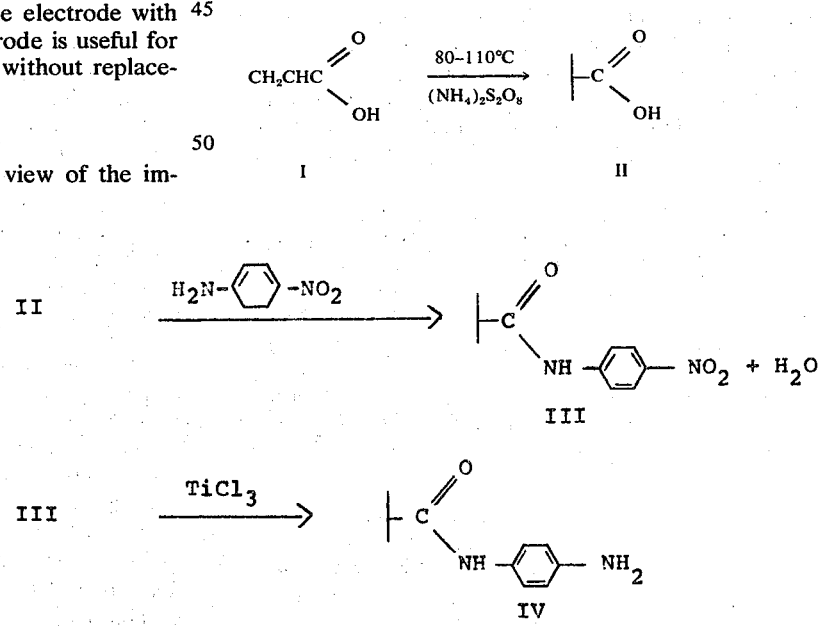

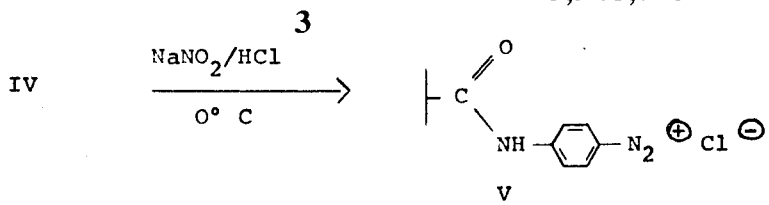

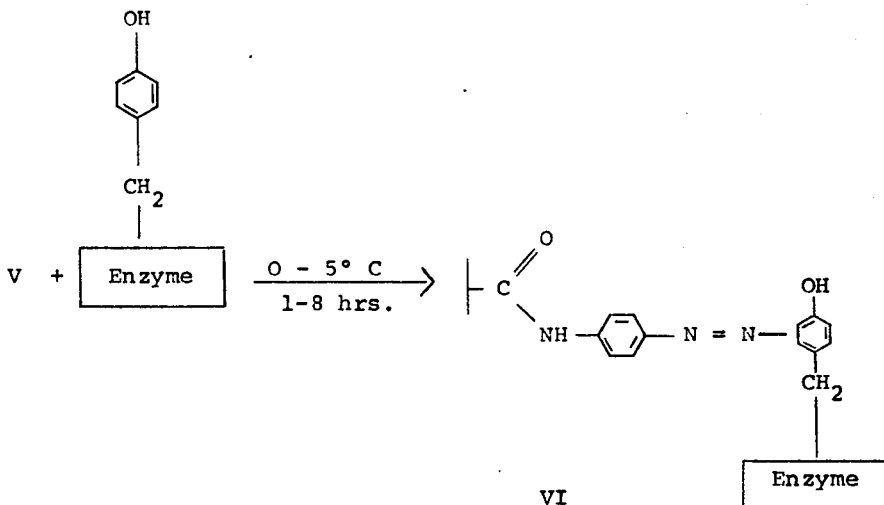

Acrylic acid is polymerized by heating with a few mg of ammonium persulfate at 80°–110° C for several hours. The viscous polyacrylic acid formed (II) is then saturated with p-nitro-aniline by stirring overnight with an excess. A portion of this is then diluted with an equal part of water. The nitro group on (III) is then reduced by adding titanium-trichloride (26%) dropwise with vigorous stirring. When reduction is complete the yellow-orange color of (III) which is soluble is completely changed to a blueblack precipitate (IV). The precipitate is then washed several times with water and then cold (0° C) 2 M nitrous acid is added slowly with vigorous stirring until the blue-black polymer (IV) completely turns white. The diazonium derivative formed (V) is quickly washed several times with cold 0.1 M phosphate or acetate buffer pH 6.0. A cold glucose oxidase solution is then added and the mixture is stirred for one to eight hours in an ice bath, after which the precipitate is washed several times with cold buffer solution.

The mode of operation of the electrode assembly 10 may be illustrated in regard to analysis for glucose content, wherein the layer 20 compriss glucose oxidase chemically bound, for example, to either the polyacrylamide derivative or the polyacrylic acid derivative described above. The electrode assembly is placed in a solution of glucose and a potential of 0.6 volts versus S.C.E. is impressed across the electrode. Glucose diffuses from the solution through the cellophane membrane 22 and into the layer 20 where it undergoes hydrolysis according to the reaction:

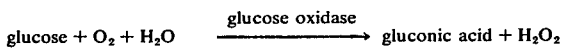

The hydrogen peroxide formed diffuses both out of the layer 20 and towards the face 16 of the platinum electrode 14 where it is oxidised. A current is produced that is proportional to the concentration of hydrogen peroxide and thus to the initial concentration of glucose. Both the initial rate of formation of hydrogen peroxide (within 4–12 seconds reaction time) and the steady state current (at 1 minute reaction time) can be used as a measure of the glucose concentration. When interferences are present that give a significant background current, the rate method would be the method of choice, because background current has no effect on the measurement of a rate. The steady state current method can also be used successfully with background current if another electrode similar to the enzyme electrode, but without the enzyme is used in parallel with the enzyme electrode and its response substracted from the glucose electrode response by means of a differential amplifier or some other subtracting technique.

The output can be automated by using operational amplifier circuitry to take the derivative of the current signal as a function of time and using further transistorized circuitry to detect and display the maximum value of the rate within the first fifteen seconds of reaction time. In the case of steady state values, the circuitry can be set to display the value of the current at one minute of reaction time.

The electrode assembly of the present invention may also be used to analyze solutions for other substances which are acted upon by enzymes to yield hydrogen peroxide or other amperometrically active substances by employing the appropriate enzyme in the layer 20. For example, it may be used to measure ascorbic acid by using the enzyme ascorbic acid oxidase, uric acid by using the enzyme uric acid oxidase, amino acid by using the appropriate amino acid oxidase, xanthine by using the enzyme xanthine oxidase, etc.

It has been found that employing the enzyme in chemically bound form in accordance with the present invention greatly improves the stability of the enzyme and makes the electrode useful for substantially greater periods of time without replacement of the enzyme portion, in comparison with enzyme electrodes in which the enzyme is in the form of a solution or merely physically bound to a solid matrix. For example, it has been found that such improvement in long term stability is greater than 50% with respect to the physically bound enzyme, and on the order of around 600% with respect to the enzyme solution.

What is claimed is:

1. An electrode assembly for use in amperometric analysis of a glucose solution comprising electrically insulating support means, a platinum electrode mounted in said support means and having an active exposed working face, a layer of solid polymeric material comprising a diazo derivative of polyacrylic acid covering said working face of said electrode, said polymeric material having glucose oxidase chemically bound thereto, and a cellophane membrane covering said layer of solid polymeric material and holding said layer in contact with said working face of said electrode.

* * * * *